US011266194B2

(12) United States Patent
Danko

(10) Patent No.: US 11,266,194 B2
(45) Date of Patent: Mar. 8, 2022

(54) BRIM SHADE AND HINGE

(71) Applicant: Danko Innovations LLC, Bradenton, FL (US)

(72) Inventor: James E. Danko, Bradenton, FL (US)

( * ) Notice: Subject to any disclaimer, the term of this patent is extended or adjusted under 35 U.S.C. 154(b) by 4 days.

(21) Appl. No.: 15/444,215

(22) Filed: Feb. 27, 2017

(65) Prior Publication Data

US 2017/0245574 A1 Aug. 31, 2017

Related U.S. Application Data

(60) Provisional application No. 62/300,116, filed on Feb. 26, 2016.

(51) Int. Cl.
*A42B 1/0184* (2021.01)
*A42B 3/04* (2006.01)
*A42B 1/24* (2021.01)
*A42B 3/18* (2006.01)
*A42B 1/242* (2021.01)
*A42B 3/22* (2006.01)
*A42B 1/247* (2021.01)
*A42B 1/18* (2006.01)
*A61F 9/04* (2006.01)
*G02C 3/02* (2006.01)
*A61F 9/02* (2006.01)

(52) U.S. Cl.
CPC .......... *A42B 1/0184* (2021.01); *A42B 3/0406* (2013.01); *A42B 1/18* (2013.01); *A42B 1/24* (2013.01); *A42B 1/242* (2013.01); *A42B 1/247* (2013.01); *A42B 3/04* (2013.01); *A42B 3/18* (2013.01); *A42B 3/185* (2013.01); *A42B 3/222* (2013.01); *A42B 3/223* (2013.01); *A61F 9/025* (2013.01); *A61F 9/045* (2013.01); *G02C 3/02* (2013.01); *Y10T 24/1391* (2015.01); *Y10T 24/1394* (2015.01)

(58) Field of Classification Search
CPC ......... A42B 1/064; A42B 1/065; A42B 1/242; A42B 1/247; A42B 1/18; A42B 3/0406; A42B 3/04; A42B 3/222; A42B 3/223; A42B 3/18; A42B 3/185; A42B 1/0184; A42B 1/24; G02C 3/02; A61F 9/045; A61F 9/025; Y10T 24/1394; Y10T 24/1391
USPC .................................................. 2/10, 12, 13
See application file for complete search history.

(56) References Cited

U.S. PATENT DOCUMENTS

| | | | | |
|---|---|---|---|---|
| 1,228,341 A | * | 5/1917 | Maynard ................ | A42B 1/247 2/10 |
| 1,502,820 A | * | 7/1924 | Funk ........................ | G02C 7/10 2/453 |
| 1,665,513 A | * | 4/1928 | Thomas .................. | A42B 1/247 2/10 |
| 1,833,741 A | * | 11/1931 | Diehl ....................... | G02C 3/02 2/10 |
| 3,781,560 A | * | 12/1973 | DeBurgh ................ | G02B 23/12 250/333 |
| 4,815,838 A | | 3/1989 | Liautaud | |

(Continued)

*Primary Examiner* — Khaled Annis
*Assistant Examiner* — Dakota Marin
(74) *Attorney, Agent, or Firm* — Michael L. Leetzow, P.A.

(57) ABSTRACT

A brim shade has a shade element, a clip, and a hinge that joins the shade element and the clip to make the brim shade. The shade element and the hinge combine to create a shade that does not allow the light to get past the brim shade. The brim shade can be adjusted through 360 degree rotation and along the side of a hat to provide protection to the wearer.

19 Claims, 15 Drawing Sheets

(56) References Cited

U.S. PATENT DOCUMENTS

| | | | |
|---|---|---|---|
| 4,869,586 A * | 9/1989 | Chung | A42B 1/247 351/158 |
| 4,951,316 A | 8/1990 | Moody | |
| 5,052,054 A | 10/1991 | Birum | |
| 5,208,916 A * | 5/1993 | Kelman | A42B 1/247 2/10 |
| 5,261,124 A | 11/1993 | Day | |
| 5,412,812 A | 5/1995 | Gatchalian | |
| 5,422,686 A | 6/1995 | Kelman et al. | |
| 5,533,208 A | 7/1996 | Tonoyan et al. | |
| 5,615,413 A | 4/1997 | Bower | |
| 5,692,234 A | 12/1997 | Yuen | |
| 5,720,040 A * | 2/1998 | Simone | G02C 3/02 2/10 |
| 5,819,311 A | 10/1998 | Lo | |
| 5,884,334 A | 3/1999 | Collette et al. | |
| 5,987,640 A * | 11/1999 | Ryder | G02C 3/02 2/10 |
| 6,247,205 B1 * | 6/2001 | Damadian | A42B 1/247 2/10 |
| 6,550,064 B2 | 4/2003 | Schmitt et al. | |
| 6,595,635 B2 * | 7/2003 | Schubert | A42B 1/247 24/3.12 |
| 6,641,266 B1 * | 11/2003 | Lazarus | A42B 1/247 2/10 |
| 6,959,989 B2 | 11/2005 | Holm | |
| 7,441,737 B2 * | 10/2008 | Bae Park | A42B 1/247 16/334 |
| 9,696,552 B1 * | 7/2017 | Goergen | A42B 1/24 |
| 2002/0021566 A1 * | 2/2002 | Lee | A42B 1/242 362/190 |
| 2003/0019005 A1 | 1/2003 | Burnett | |
| 2003/0071961 A1 * | 4/2003 | Schubert | A42B 1/247 351/57 |
| 2004/0093654 A1 * | 5/2004 | Hanrahan | A61F 9/045 2/12 |
| 2005/0039240 A1 * | 2/2005 | Kidouchim | A61F 9/04 2/10 |
| 2009/0229028 A1 | 9/2009 | Dobkins | |
| 2009/0307816 A1 * | 12/2009 | Stachler | A42B 3/185 2/10 |
| 2012/0099196 A1 * | 4/2012 | Wood | A42B 1/247 359/480 |

* cited by examiner

BRIM SHADE AND HINGE

REFERENCE TO RELATED CASE

This application claims priority under 35 U.S.C. § 119 (e) to provisional application No. 62/300,116 filed on Feb. 26, 2016, the contents of which are hereby incorporated by reference in their entirety.

FIELD OF THE INVENTION

In sunny locales, many people wear hats to keep the sun out of their eyes and off their faces. Many times the hats are ball caps or other caps that have a visor or brim. While the visor or brim of the hat may assist when the sun is high in the sky or in the direction the person is looking, that may not always be the case. Indeed, the sun may be off to one side or lower in the sky. Such a position may make it difficult to block the sun from entering the person's eyes. Sunglasses may also be sufficient to block the sun or reflections from the sun. The brim of the hat can not be changed to accommodate such a situation. And while a baseball cap can be re-arranged to some extent, it may not always be possible to block those rays. Use of a towel or a second hat is less than ideal as they can easily shift or fall off.

Thus, a movable shade that can block the sun's rays from entering the eyes of a person wearing a hat is needed. The shade also needs to be able to be moved out of the way when it is not needed. Such a device is illustrated and described below.

SUMMARY OF THE INVENTION

The present invention is directed to a brim shade that includes a shade element, a clip configured to be removably attached to a brim of a hat, a hinge having a first axis of rotation and a second axis of rotation, the first and second axes being parallel to one another, the hinge having a first portion operatively connected to the shade element and a second portion operatively connected to the clip, wherein the shade element is rotatable between a first and second position through an angle, the angle being at least 350 degrees.

In some embodiments, the opening has a longitudinal axis therethrough and the clip has an outside surface, there being a first distance between the longitudinal axis and the outside surface of the clip and a second distance between the first axis of rotation and the second axis of rotation, the second distance being greater than the first distance.

In some other embodiments, the the hinge includes a coiled spring pin.

According to another embodiment, there is a hinge that includes a first cylindrical member, the first cylindrical member having a first opening extending through the first cylindrical member along a first longitudinal axis, a second cylindrical member connected to the first cylindrical member, the second cylindrical member having a second opening extending through the first cylindrical member along a second longitudinal axis, the first and second longitudinal axes being parallel to one another, a first cut-out in the first cylindrical member to receive at least a portion of a clip therein, and at least one cut-out in the second cylindrical member to receive at least a portion of a shade element therein.

In some other embodiments, the at least one cut-out comprises two cut-outs and the cut-out in the first cylindrical member is disposed between the two cut-outs in the second cylindrical member.

It is to be understood that both the foregoing general description and the following detailed description of the present embodiments of the invention are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and, together with the description, serve to explain the principles and operations of the invention.

DETAILED DESCRIPTION OF THE PREFERRED EMBODIMENTS

Figure 1:
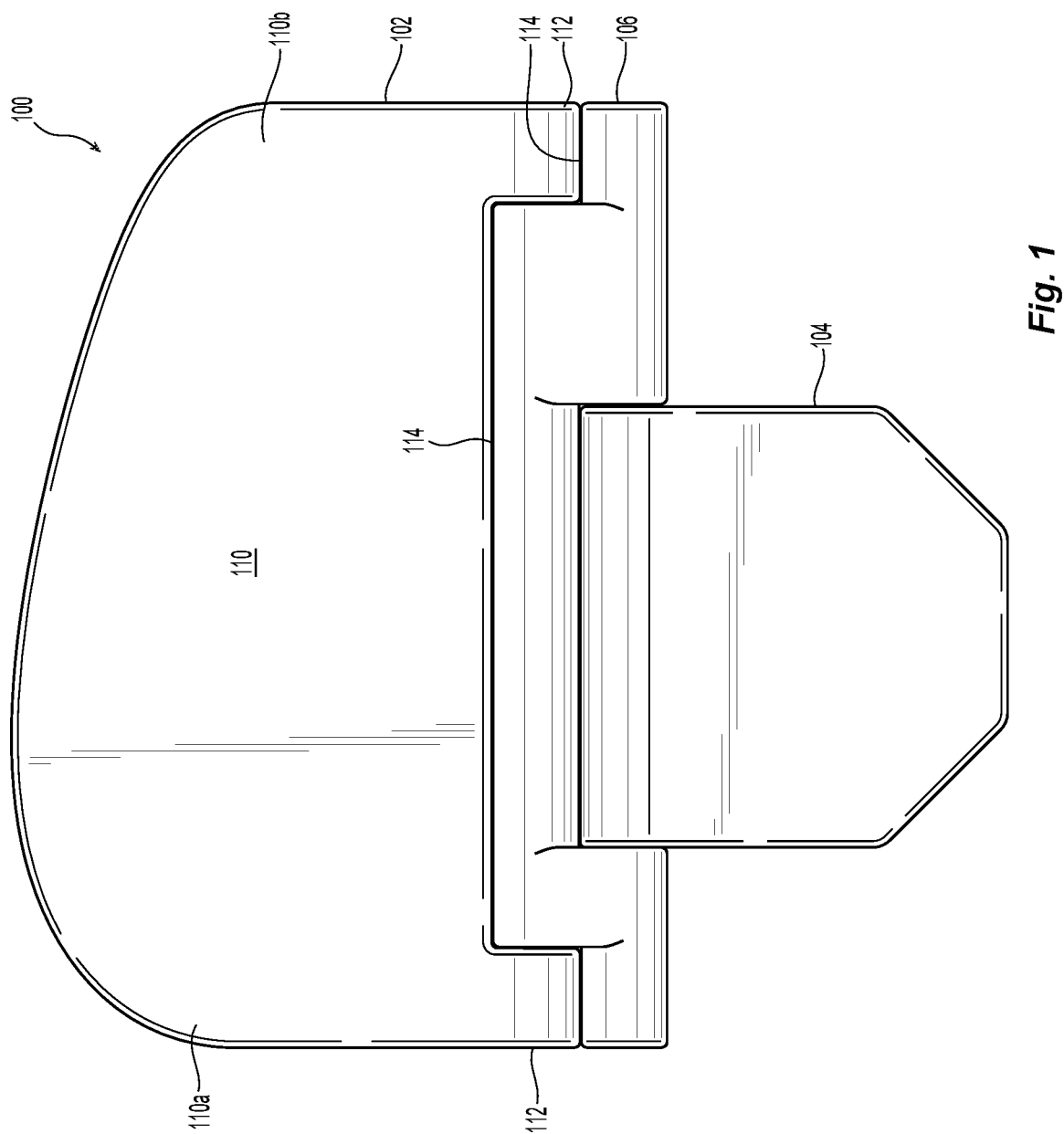
FIG. 1 is a top of one embodiment the brim shade according to the present invention.

Reference will now be made in detail to the present preferred embodiment(s) of the invention, examples of which are illustrated in the accompanying drawings. Whenever possible, the same reference numerals will be used throughout the drawings to refer to the same or like parts.

Referring to the figures, one embodiment of a brim shade 100 according to the present invention is preferably comprised of three components. The brim shade has a shade element 102, a clip 104, and a hinge 106 that joins the shade element 102 and the clip 104 to make the brim shade 100. It may also be made of any type of material deemed appropriate for providing shade or protection such as cloth, plastic or metal. The materials may be tinted, translucent or opaque and come in an unlimited number of colors. The shade element 102 has a large flat portion 110 that transitions into a cylindrical portion 112 at one edge 114 to join with the hinge 106. The edge 114 at the hinge 106 has a width W1 that is the same as the width W2 of the hinge 106. The large flat portion 110 of shade element 102 may have any shape, but is illustrated to provide a larger area 110*a* where the user's eyes would be and a smaller area 110*b* where the shade element 102 would be position near the user's ear or side of the face. The large flat portion 110 may be of any shape and size and still fall within the scope of the present invention. See also FIG. 15 for another shape as a non-limiting example. The particular thickness t1 of the shade element 102 is not critical except that it should not be flimsy or break easily. The width W1 is preferably the same as the width W2 of the hinge 106 so to prevent any gaps in the protection of the person using the brim shade 100 as described in more detail below.

Figure 2:
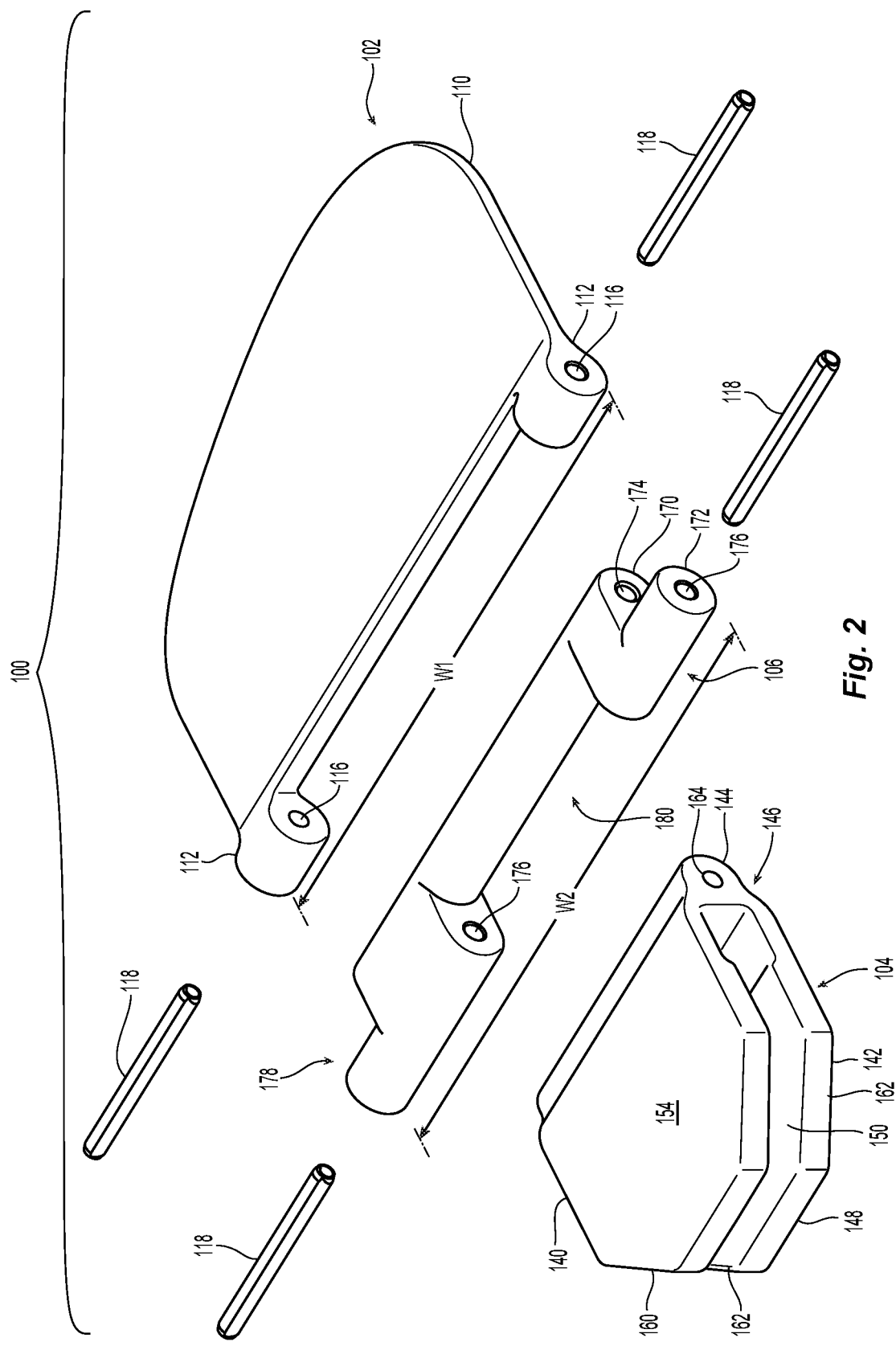
FIG. 2 is an exploded perspective view of the brim shade of FIG. 1.
Figure 3:
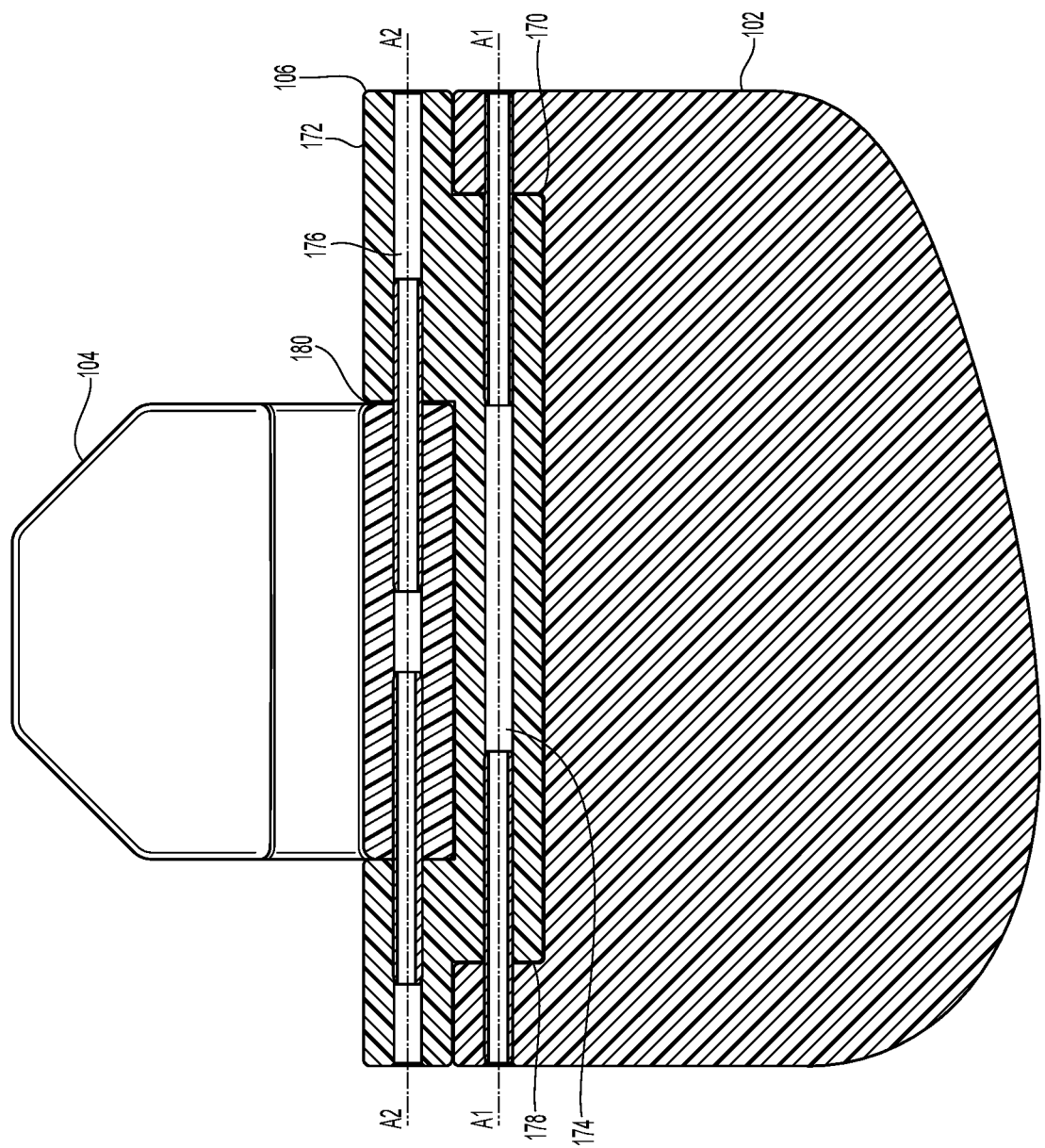
FIG. 3 is a cross sectional view of the brim shade of FIG. 1.

The shade element 102 has two cylindrical portions 112 at either end of edge 114 as best illustrated in FIGS. 1-3. These cylindrical portions 112 are at either end of the edge 114, but could be disposed anywhere along the edge 114 as long as the clip 104 and the hinge 106 were to be configured to accept the new configuration and prevent light (or water, etc.) from passing through gaps in the brim shade 100. The cylindrical portions 112 have a central opening 116 to receive a pin 118 therein to allow the shade element 102 to rotate relative to the hinge 106 and the clip 104, as discussed below. Preferably, the pin 118 is a coiled spring pin to allow for the relative positions of the brim shade 100 elements to be at any angle, as illustrated in some of the figures (See, e.g., FIGS. 6-14) and discussed in detail below. However, the pin 118 could be any type of pin, including a slotted pin.

Figure 4:
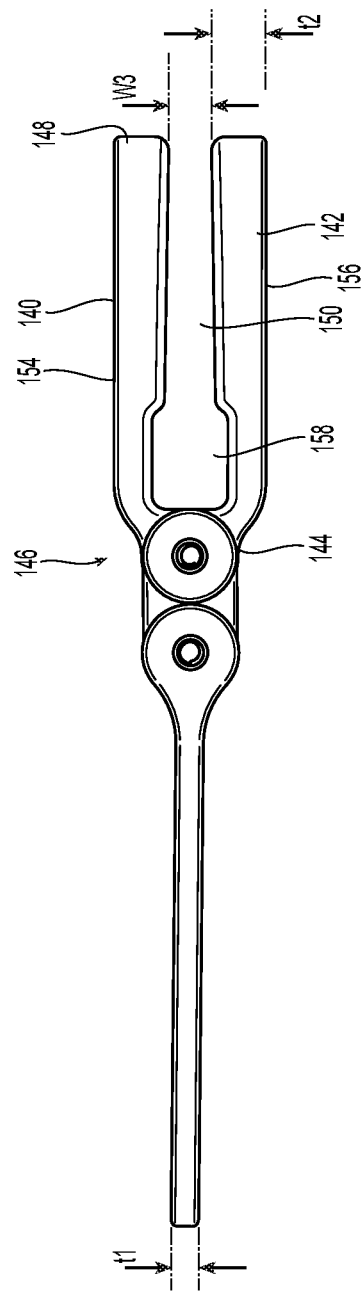
FIG. 4 is a side view of the brim shade of FIG. 1.
Figure 5:
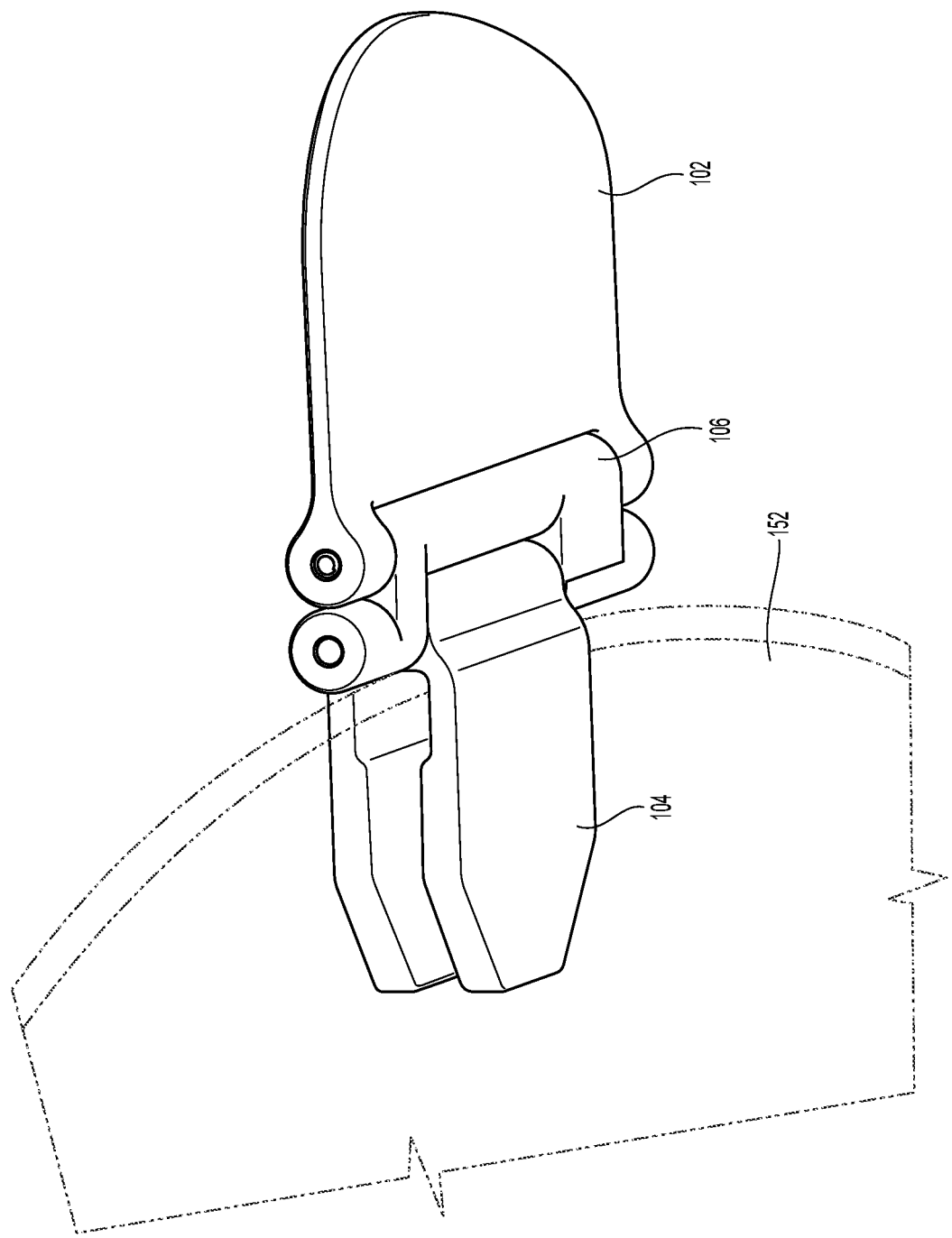
FIG. 5 is an underside view of the brim shade of FIG. 1 attached to a brim of a hat.
Figure 6:
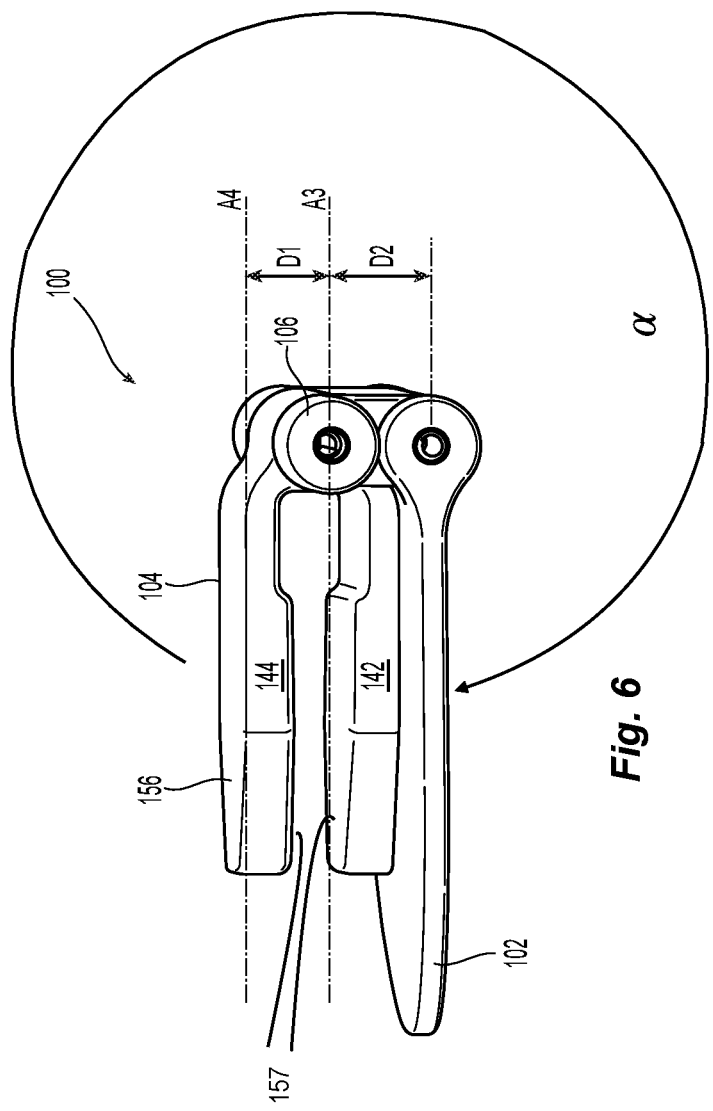
FIG. 6 is a side perspective view of the brim shade of FIG. 1 in a first position.

The clip 104 of the brim shade 100 has two extensions 140,142 extending from a base 144 at a proximal portion 146 to a distal end 148. The two extensions 140,142 form an opening 150 along the clip 104 to receive a portion of the brim 152 of the hat. See FIG. 5. As illustrated in FIG. 4, the opening has a width W3 that decreases in size between the proximal portion 146 to the distal end 148. This allows for a tighter attachment to the brim 152. Additionally, as is visible in FIG. 4, the thickness t2 of the two extensions 140,142 increases between the proximal portion 146 to the distal end 148. This is a result of the outside surfaces 154,156 being parallel to one another while the opening 150 decreases in width due to projections 157. However, two extensions 140,142 could also be of constant thickness, meaning that the outside surfaces 154,156 would not parallel to one another. At the proximal end 146 of the two extensions 140,142 is a squared-shape portion 158 of the opening 150. This squared-shape portion 158 could also have other shapes, e.g., oval, round, etc. and still fall within the scope of the present invention. The squared-shape portion 158 of the opening 150 is configured to receive the edge of the brim 152 of the hat. See FIG. 5. This allows for the two extensions 140,142 to engage the brim 152 of the hat without the thicker edge of the brim preventing the two extensions 140,142 from securely engaging the brim 152.

Figure 15:
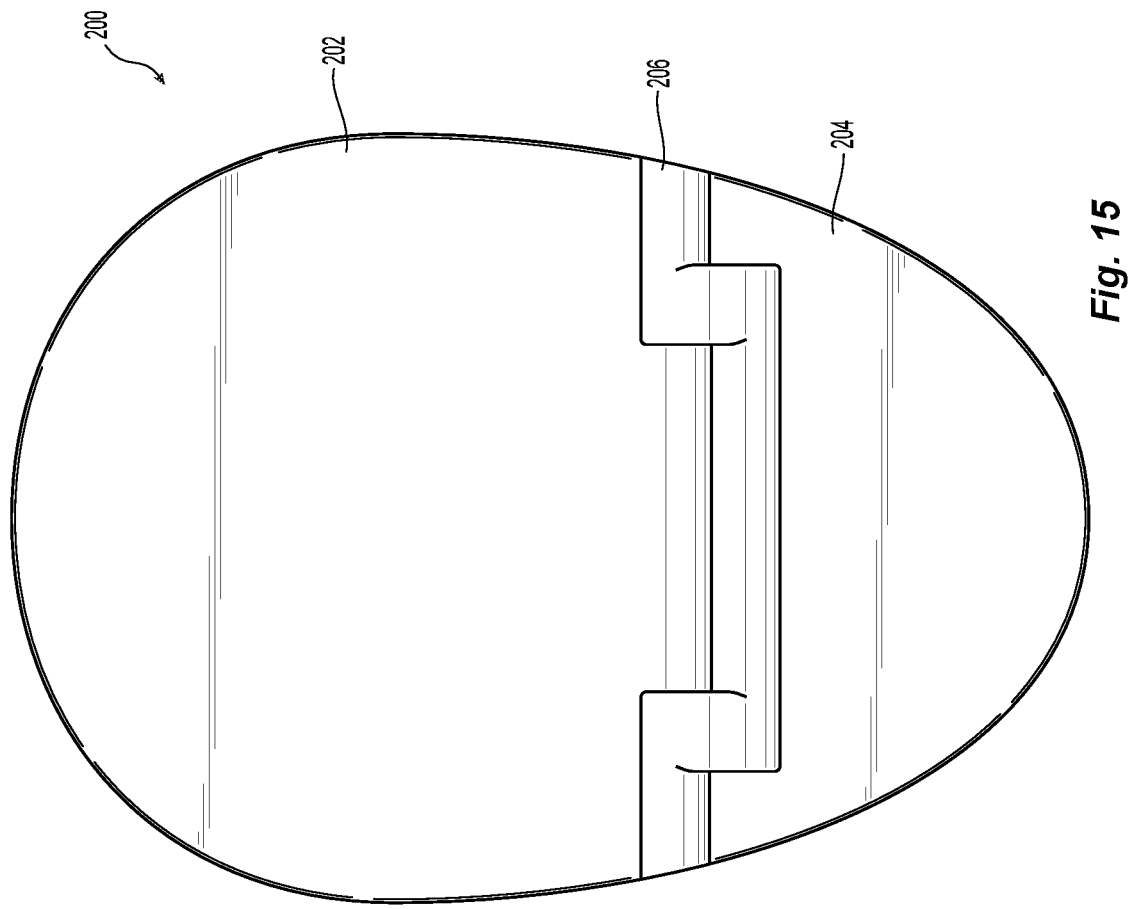
FIG. 15 is a top view of another embodiment of a brim shade according to the present invention.

As best seen in FIGS. 1 & 3, the two extensions 140,142 have truncated corners 160,162 at the distal end 148. These truncations 160,162 are illustrated to be 45 degree corners, but could be any appropriate angle. Additionally, only one of the corners of each of the extensions 140,142 may be truncated and still fall within the scope of the present invention. The truncated corners 160,162 allow the brim shade 100 to be adjusted along the brim 152 of the hat in more positions than if the corners 160,162 were not truncated. The truncated corners 160,162 allow the brim shade 100 to be pushed farther back on the brim 152 of a baseball cap than if they were not truncated. Thus, specific angles could be used for specific hats. Additionally, as illustrated in FIG. 15 (egg shaped), the extensions (as well as the other elements of the brim shade) could have other configurations.

The base 144 of the clip 104 is a cylindrical portion with a pin opening 164 to receive another coiled spring pin 118. The base 144 of the clip 104 has a width that is the same as that of the two extensions 140,142. However, as would be clear to one of skill in the art, they do not have to be same width, as long as there were no gaps caused between the hinge 106 and the shade element 102. Thus the two extensions 140,142 or the base 144 could be wider. Additionally, the clip 104 could also be disposed along the length of the shade element 102 in a position different from that illustrated in the figures, with appropriate changes made to the construction of the shade element 102 and the hinge 106.

The clip 104 is preferably made from a material that is somewhat flexible to allow for the brim 152 of the hat to be inserted between the two extensions 140,142 (thereby causing them to flex outward and away from one another and then back to engage the brim 152 to hold the brim shade 100 on the hat).

The hinge 106 is generally two cylindrical portions 170, 172 joined together with their longitudinal axes A1, A2 parallel to one another. Also along the longitudinal axes of each of the cylindrical portions 170, 172 are pin openings 174, 176 to receive a coiled spring pin 118 in each. To attach the other portions of the brim shade 100 to the hinge 106, there are cut out portions 178,180, respectively to receive the corresponding cylindrical portions from the shade element 102 and the clip 104. As the cylindrical portions 112 are at either end of the edge 114 in the shade element 102, the cut out portions 178 are at the ends of the cylindrical portion 170. With the clip 104 having only one cylindrical portion at the base 144, the cut out portion 180 is towards the middle of the cylindrical portion 172 of the hinge 106.

Figure 7:
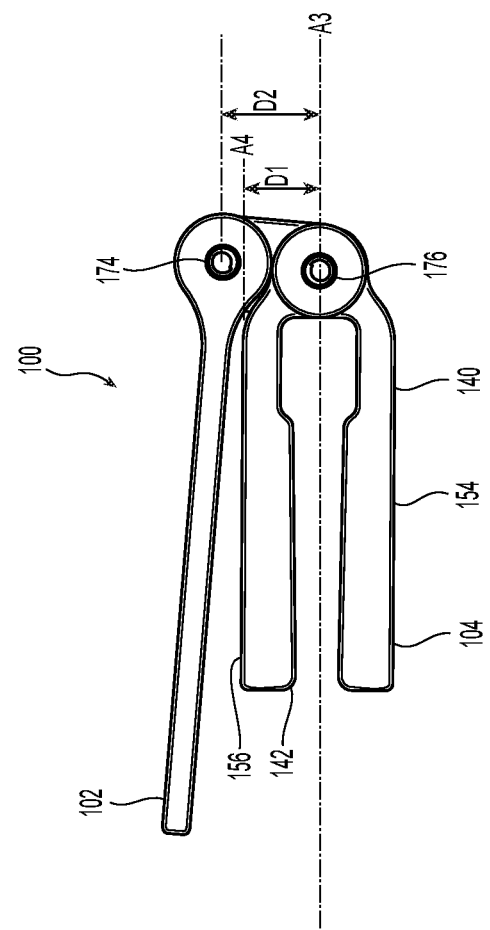
FIG. 7 is a side view of the brim shade in FIG. 1 in a second position.
Figure 8:
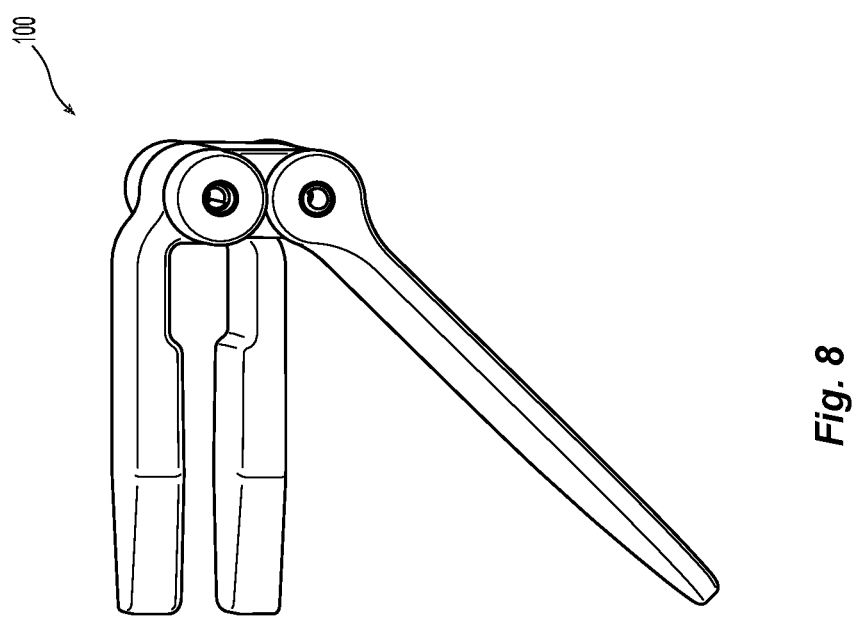
FIGS. 8-14 are perspective side views of the brim shade in FIG. 1 with the elements in different rotational positions.
Figure 9:
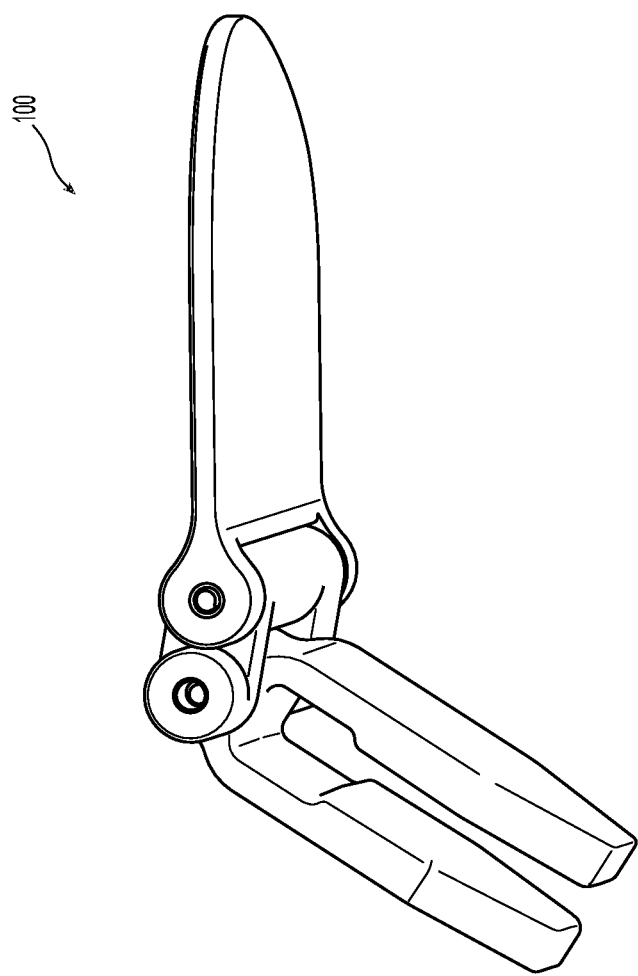
Figure 10:
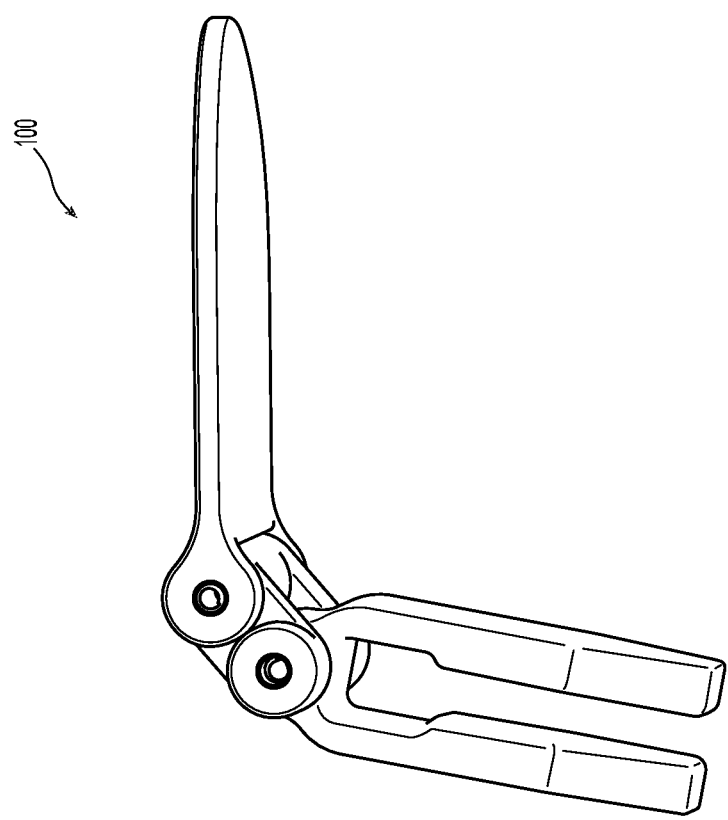
Figure 11:
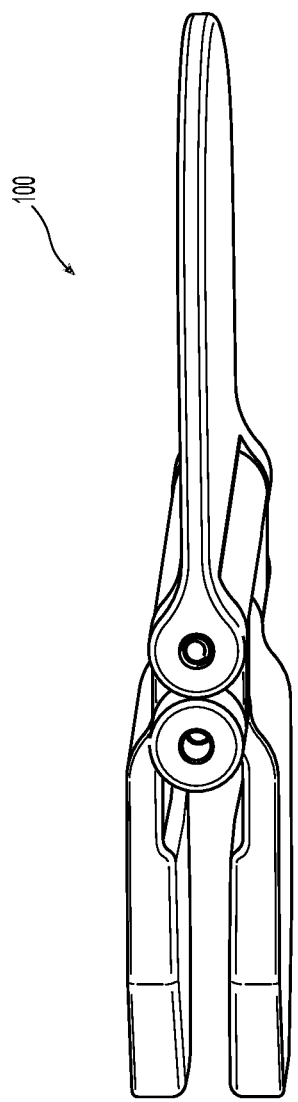
Figure 12:
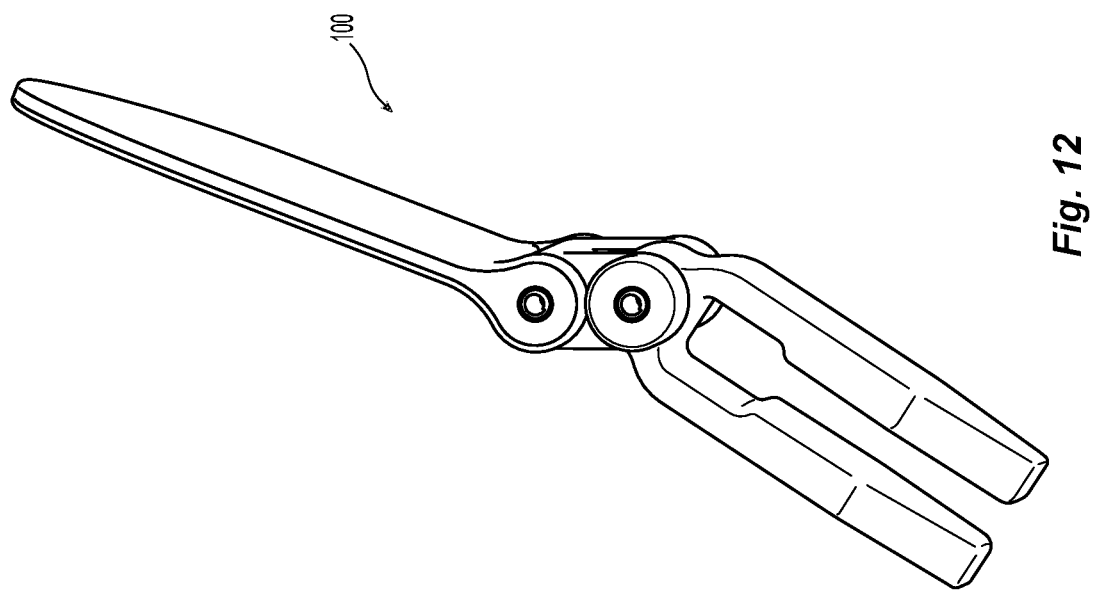
Figure 13:
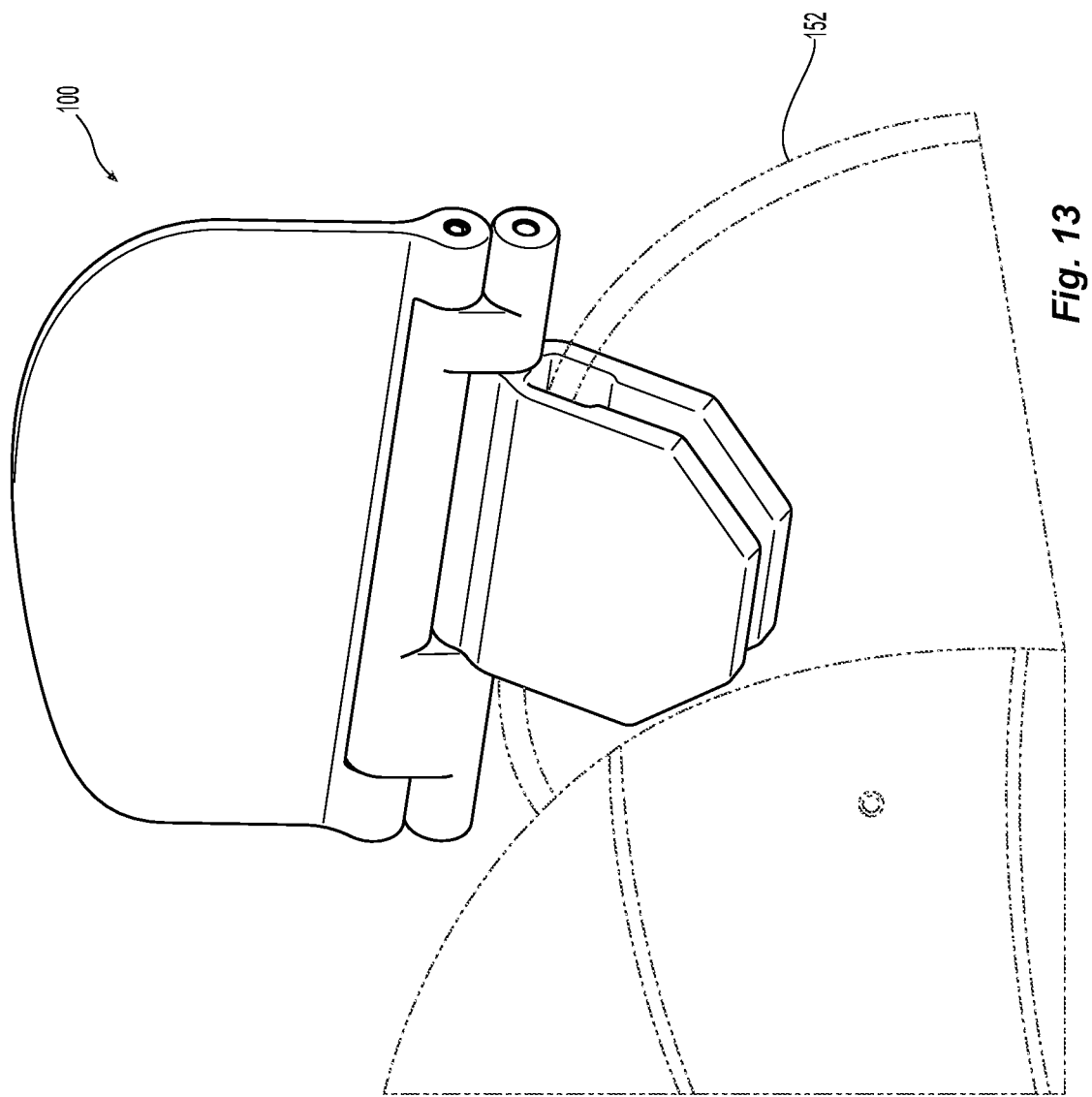
Figure 14:
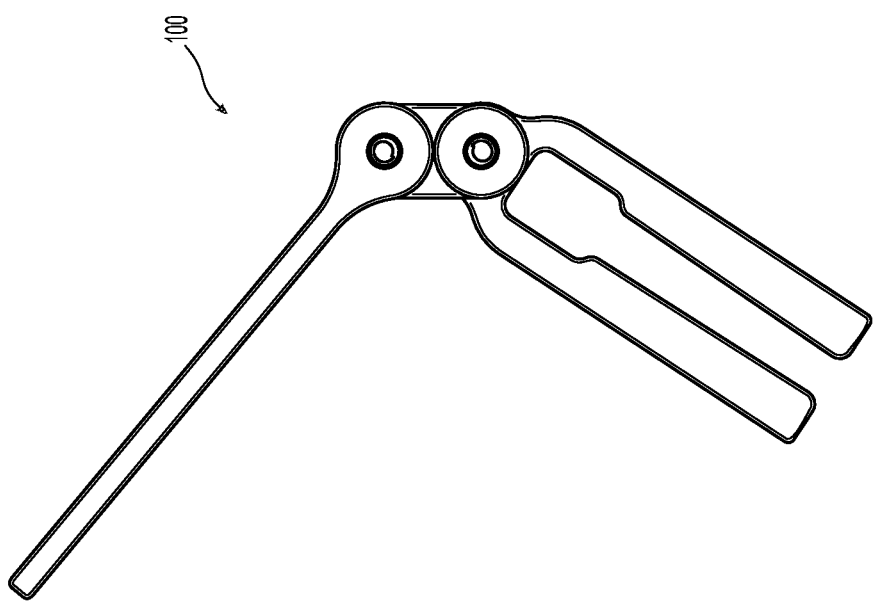

As noted above, the brim shade 100 can be used on either side of a hat, as well as being stored under the brim 152 of the hat or on top of the brim 152 of the hat. The construction of the brim shade 100, and the hinge 106 in particular, allows for the rotation of the shade element 102 and, in part, the hinge 106, relative to the clip 104. The rotation of the shade element 102 between and underneath position and an on-top position will be explained with reference to FIGS. 6 and 7. These two figures show the brim shade 100 in a first position in FIG. 6—under the brim, which is not shown for clarity purposes, and then in second position in FIG. 7—on-top of the brim. Thus, the shade element 102 can rotate through an angle α of 360 degrees (and possibly farther) so that it would be parallel to the outside surfaces 154,156 of the clip 106. The rotation through the 360 degree angle is due to the construction of the hinge 106. As best illustrated in FIG. 7, the opening 150 has a longitudinal axis A3 extending therethrough. This axis is parallel to the axis A4 that is parallel to the outside surfaces 154,156 of the clip 106. There is a distance D1 between the axis A3 and the axis A4 that aligns with the outside surfaces 154,156 of the clip 106. Each of the two cylindrical portions 170,172 have an axis of rotation about the openings 174 and 176. As is clear from FIG. 7, the opening 176 is on the longitudinal axis A3. The other axis of rotation is through the second opening 174 and the distance between these two openings (and axis of rotations) is illustrated as being D2. If D2 is larger than D1, then the shade element 102 can rotate at least 360 degrees around the axis of rotation about opening 176.

FIGS. 8-14 show various positions of the three elements of the brim shade 100 (shade element 102, a clip 104, and a hinge 106) as the shade element 102 is rotated around from the first position to the second position—360 degree angle relative to the clip 104. Careful consideration of these figures show that the clip 106 and the shade element 102 can both rotate about their axis of rotations independently of the other.

FIG. 15 illustrates another embodiment of a brim shade 200 according to the present invention. This embodiment 200 illustrates the different variations in shape of the three elements (shade element 202, a clip 204, and a hinge 206) that still fill all of space between the three elements and prevent light from entering between the three elements.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

I claim:

1. A brim shade comprising:
   an opaque shade element having a first flat side and an opposing second flat side, and at least one pin opening along an edge thereof to receive a first pin therein;
   a clip configured to be removably attached to a brim of a hat, the clip having a pin opening along a base portion to receive a second pin;
   a hinge having a first portion having a first longitudinal axis and a second portion having a second longitudinal axis, the first longitudinal axis and the second longitudinal axis being parallel to one another, each of the first portion and second portion having a pin opening extending therethrough and parallel to the respective longitudinal axis and wherein the pin opening in the first portion is aligned with the at least one pin opening of the opaque shade element and the pin opening in the second portion is aligned with the pin opening in the clip;
   wherein the opaque shade element is rotatable between a first and second position through an angle, the angle being at least 350 degrees.

2. The brim shade according to claim 1, wherein the first flat side and second flat side of the opaque shade element are larger than an outside surface of the clip.

3. The brim shade according to claim 1, wherein the opaque shade element has a first width and the hinge has a second width, the first and the second widths being the same.

4. The brim shade according to claim 1, wherein the opaque shade element has a configuration other than rectangular.

5. The brim shade according to claim 1, wherein the first pin and the second pin are both a coiled spring pin.

6. The brim shade according to claim 1, wherein the pin opening in the first portion of the hinge and the at least one pin opening of the opaque shade element receive at least a portion of the first pin, and the pin opening in the second portion of the hinge and the pin opening in the clip receives at least a portion of the second pin.

7. The brim shade according to claim 1, wherein the at least one pin opening in the opaque shade element comprises two pin openings, the two pin openings spaced along an edge of the opaque shade element.

8. The brim shade according to claim 1, wherein the pin openings in each of the opaque shade, clip and hinge are enclosed circles in cross section.

9. The brim shade according to claim 1, wherein the at least one pin opening in the opaque shade element is in a cylindrical portion, the first flat side and the second flat side transitioning into the cylindrical portion.

10. The brim shade according to claim 1, wherein the second portion of the hinge has a first cut out, the first cut out separating the pin opening into two separate pin openings.

11. The brim shade according to claim 3, wherein the first portion of the hinge has a cut-out at each end, thereby making the pin opening in the first portion of the hinge shorter than the first width of the opaque shade element.

12. The brim shade according to claim 1, wherein the opaque shade element is rotatable between a first and second position through an angle, the angle being at least 350 degrees.

13. A brim shade comprising:
    a shade element having a first side, a second side, and at least one pin opening along an edge thereof to receive a first pin therein;
    a clip configured to be removably attached to the brim of a hat, the clip having a pin opening along a base portion to receive a second pin; and
    a hinge having a first portion having a first longitudinal axis and a second portion having a second longitudinal axis, the first longitudinal axis and the second longitudinal axis being parallel to one another, each of the first portion and second portion having a pin opening extending therethrough and parallel to the respective longitudinal axis and wherein the first pin is inserted into the first portion of the hinge and into the opaque shade element, and the second pin is inserted into the second portion of the hinge and the pin opening in the clip; wherein the shade element is rotatable between a first and second position through an angle, the angle being at least 350 degrees.

14. The brim shade according to claim 13, wherein the pin opening in the first portion of the hinge and the at least one pin opening of the opaque shade element receive at least a portion of the first pin, and the pin opening in the second portion of the hinge and the pin opening in the clip receives at least a portion of the second pin.

15. The brim shade according to claim 13, wherein the at least one pin opening in the opaque shade element comprises two pin openings, the two pin openings spaced along an edge of the opaque shade element.

16. The brim shade according to claim 13, wherein the pin openings in each of the shade, clip and hinge are enclosed circles in cross section.

17. The brim shade according to claim 13, wherein the at least one pin opening in the opaque shade element is in a cylindrical portion, the first flat side and the second flat side transitioning into the cylindrical portion.

18. The brim shade according to claim 13, wherein the second portion of the hinge has a first cut out, the first cut out separating the pin opening into two separate pin openings.

19. The brim shade according to claim 13, wherein the first portion of the hinge has a cut-out at each end, thereby making the pin opening in the first portion of the hinge shorter than the first width of the shade element.

* * * * *